US00PP26383P2

(12) United States Plant Patent
Thorup

(10) Patent No.: US PP26,383 P2
(45) Date of Patent: Feb. 2, 2016

(54) ***VIOLA* PLANT NAMED 'HALO LEMON FROST'**

(50) Latin Name: *Viola cornuta*
Varietal Denomination: Halo Lemon Frost

(71) Applicant: Ball Horticultural Company, West Chicago, IL (US)

(72) Inventor: Troy Thorup, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 26 days.

(21) Appl. No.: 14/121,364

(22) Filed: Aug. 25, 2014

(51) Int. Cl.
*A01H 5/02* (2006.01)

(52) U.S. Cl.
USPC ..... Plt./323

(58) Field of Classification Search
USPC ..... Plt./323
CPC ..... A01H 5/02; A01H 5/00
See application file for complete search history.

*Primary Examiner* — Kent L Bell
(74) *Attorney, Agent, or Firm* — Audrey Charles

(57) ABSTRACT

A new and distinct cultivar of *Viola* plant named 'Halo Lemon Frost', characterized by its bright yellow and cream colored flowers with medium violet-blue margins, medium green-colored foliage, and vigorous, mounded-spreading growth habit, is disclosed.

1 Drawing Sheet

Latin name of genus and species of plant claimed: *Viola cornuta.*

Variety denomination: 'Halo Lemon Frost'.

BACKGROUND OF THE INVENTION

The present invention relates to a new and distinct cultivar of *Viola* plant botanically known as *Viola cornuta* and hereinafter referred to by the cultivar name 'Halo Lemon Frost'.

The new cultivar originated in a controlled breeding program in Guadalupe, Calif. during April 2010. The objective of the breeding program was the development of *Viola* cultivars having large flowers with distinctive flower coloration and a mounded-spreading growth habit.

The new *Viola* cultivar is the result of cross-pollination. The female (seed) parent of the new cultivar is the proprietary *Viola cornuta* breeding selection coded 08-22123-1, not patented, characterized by its light yellow-colored flowers with light violet-blue margins, medium green-colored foliage, and vigorous, trailing growth habit. The male (pollen) parent of the new cultivar is the proprietary *Viola cornuta* breeding selection coded 08-22094-1, not patented, characterized by its light yellow-colored flowers with dark violet-blue margins, medium green-colored foliage, and moderately vigorous, mounded growth habit. The new cultivar was discovered and selected as a single flowering plant within the progeny of the above stated cross-pollination during October 2010 in a controlled environment in Guadalupe, Calif.

Asexual reproduction of the new cultivar by terminal stem cuttings since October 2010 in Guadalupe, Calif. and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Halo Lemon Frost' as a new and distinct cultivar of *Viola* plant:

1. Bright yellow and cream colored flowers with medium violet-blue margins;
2. Medium green-colored foliage; and
3. Vigorous, mounded-spreading growth habit.

Plants of the new cultivar differ from plants of the female parent primarily in having a darker flower margin color. Plants of the new cultivar differ from plants of the male parent primarily in having a more vigorous, spreading growth habit and a lighter flower margin color.

Of the many commercially available *Viola* cultivars, the most similar in comparison to the new cultivar is 'Halo Lilac', U.S. Plant Pat. No. 24,542. However, in comparison, plants of the new cultivar differ from plants of 'Halo Lilac' in at least the following characteristics:

1. Plants of the new cultivar have a petal color different from plants of 'Halo Lilac'; and
2. Plants of the new cultivar have a foliage color that is darker than plants of 'Halo Lilac'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Halo Lemon Frost'. The plants were grown in one-gallon containers for approximately two months in a greenhouse and one month outdoors in Elburn, Ill.

DETAILED BOTANICAL DESCRIPTION

Figure 1:
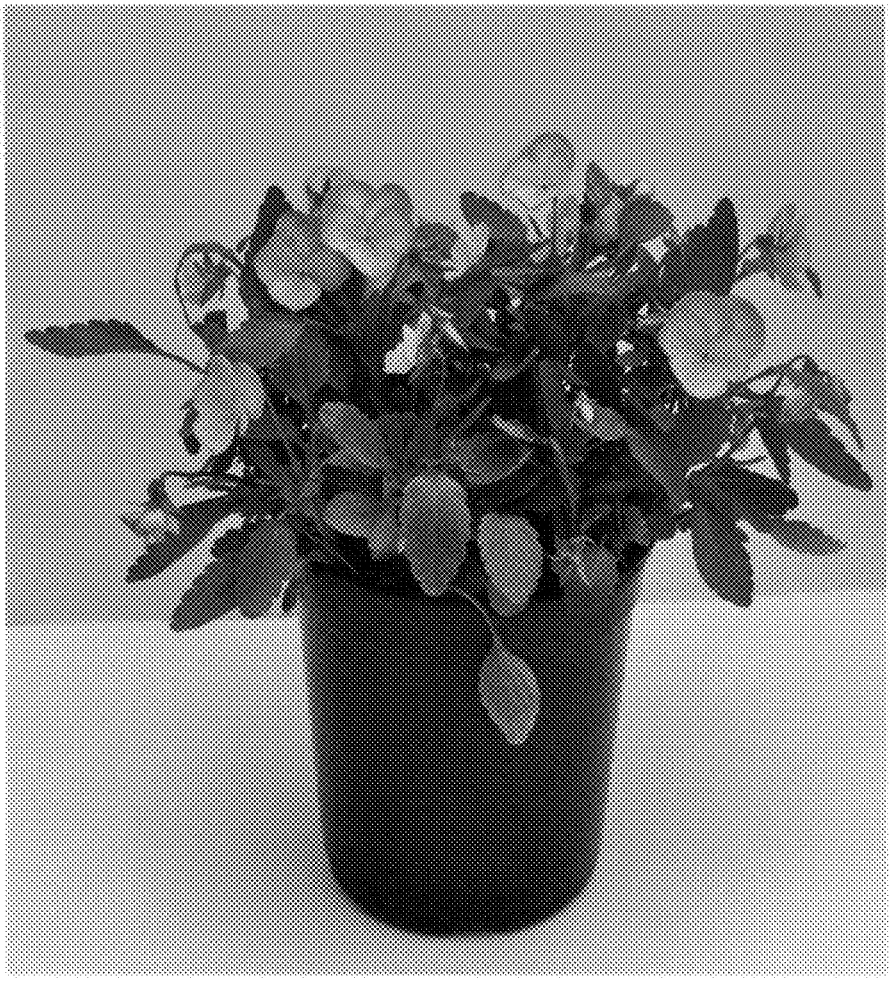
FIG. 1 illustrates a side view of the overall growth and flowering habit of 'Halo Lemon Frost'.
Figure 2:
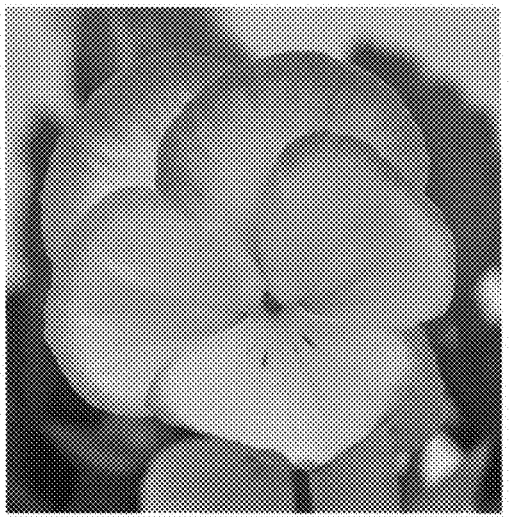
FIG. 2 illustrates a close-up view of an individual flower of 'Halo Lemon Frost'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in June 2014 under natural light conditions in West Chicago, Ill.

The following descriptions and measurements describe plants produced from cuttings from stock plants and grown in a glass-covered greenhouse under conditions comparable to those used in commercial practice. The plants were grown utilizing a soilless growth medium in one-gallon containers for approximately two months in a greenhouse and one month outdoors in Elburn, Ill. Greenhouse temperatures were maintained at approximately 45° F. to 65° F. (7.2° C. to 18.3° C.) during the day and approximately 35° F. to 45° F. (1.7° C. to 7.2° C.) during the night. No supplemental lighting was provided. Measurements and numerical values represent averages of typical plants.

Botanical classification: *Viola cornuta* cultivar Halo Lemon Frost.

Parentage:

*Female parent*.—Proprietary *Viola cornuta* breeding selection coded 08-22123-1, not patented.

*Male parent*.—Proprietary *Viola cornuta* breeding selection coded 08-22094-1, not patented.

Propagation:

*Type cutting*.—Terminal stem.

*Time to initiate roots*.—Approximately 10 to 12 days.

*Time to produce a rooted cutting*.—Approximately 24 to 28 days.

*Root description*.—Fine, fibrous.

*Rooting habit*.—Freely branching.

Plant description:

*Commercial crop time*.—Approximately 8 to 9 weeks from a rooted cutting to finish in a 10 cm pot.

*Growth habit and general appearance*.—Moderately vigorous, mounded-spreading.

*Size*.—Height from soil level to top of plant plane: Approximately 17.0 cm. Width: Approximately 32.0 cm.

*Branching habit*.—Freely basal branching. Quantity of main branches per plant: Approximately 24.

*Lateral branches*.—Strength: Strong, flexible. Length: Approximately 16.0 cm. Diameter: Approximately 4.0 mm. Length of central internode: Approximately 3.0 cm. Texture: Glabrous. Color of young and mature stems: 144C.

Foliage description:

*General description*.—Quantity of leaves per main branch: Approximately 7. Fragrance: None. Form: Simple. Arrangement: Alternate.

*Leaves*.—Aspect: Petiole is at an acute angle to stem and leaf blade is perpendicular to downward turning. Shape: Narrowly ovate. Margin: Crenate. Apex: Obtuse. Base: Attenuate to rounded. Venation pattern: Pinnate. Length of mature leaf at center of stem: Approximately 5.7 cm. Width of mature leaf at center of stem: Approximately 2.5 cm. Texture of upper and lower surfaces: Glabrous. Color of upper surface of young foliage: 146B with base of 144B and venation indistinguishable from lamina. Color of lower surface of young foliage: Closest to 138A to 138B with venation indistinguishable from lamina. Color of upper surface of mature foliage: N137B with midvein of 145A and other venation indistinguishable from lamina. Color of lower surface of mature foliage: Closest to 137B to 137C with venation of 145A.

*Petiole*.—Length: Approximately 4.8 cm. Diameter: Approximately 2.0 mm. Texture: Glabrous. Color: 144A.

*Stipules*.—Shape: Narrowly Ovate. Margin: Pinnately parted. Apex: Obtuse. Base: Obtuse. Length: Approximately 5.6 cm. Width: Approximately 2.4 cm. Texture of upper and lower surfaces: Glabrous. Color of upper surface: 137A to 137B with venation indistinguishable from lamina. Color of lower surface: Closest to 147B with venation of 144A.

Flowering description:

*Flowering habit*.—'Halo Lemon Frost' is freely flowering under outdoor growing conditions with substantially continuous blooming from spring through autumn and with limited flowering under short winter days in a greenhouse environment.

*Lastingness of individual flower on the plant*.—Approximately 5 to 7 days.

Flower description:

*General description*.—Type: Single, zygomorphic, not persistent. Flower aspect; Outward facing to pendant. Quantity per plant: Approximately 17. Fragrance: Slightly sweet.

*Bud*.—Rate of opening: Generally takes 2 to 3 days for bud to progress from first color to fully open flower. Quantity showing color per plant: Approximately 20.

*Bud just before opening*.—Shape: Oblong. Length: Approximately 1.5 cm. Diameter: Approximately 5.0 mm. Color: 150C with patches of 85D.

*Corolla*.—Shape: Orbicular, with a spur on lower petal. Length: Approximately 4.1 cm. Width: Approximately 3.9 cm. Depth: Approximately 2.9 cm.

*Petals*.—Quantity: Five in a single whorl; two upper petals, two lateral petals and one lower petal, spurred. Shape of upper and lateral petals: Obovate. Shape of lower petal: Obcordate. Appearance: Dull. Margin of all petals: Entire. Apex of upper and lateral petals: Rounded. Apex of lower petal: Obcordate. Base of all petals: Attenuate. Length of upper petals: Approximately 2.2 cm. Width of upper petals: Approximately 2.6 cm. Length of lateral petals: Approximately 2.0 cm. Width of lateral petals: Approximately 2.2 cm. Length of lower petal: Approximately 1.9 cm. Width of lower petal: Approximately 2.6 cm. Texture of upper surface: Glabrous, with base of lateral and lower petals densely glandular pubescent. Texture of lower surface: Glabrous. Color of upper surface of upper petals when first and fully open: 10D to 10A with margins of N88C. Color of lower surface of upper petals when first and fully open: Lighter than 3D with margins of 91A. Color of upper surface of lateral petals when first and fully open: 3A to 3C with margins of N88C. Color of lower surface of lateral petals when first and fully open: 3D with margins of 92B. Color of upper surface of lower petal when first and fully open: 6B to 6C with margins of N88C and base of 14B forming an eye. Color of lower surface of lower petal when first and fully open: 3D with margins of 92B.

*Spur*.—Quantity: 1 per flower. Length: Approximately 1.0 cm. Diameter at proximal end: Approximately 2.0 mm. Diameter at distal end: Approximately 1.0 mm. Color: Closest to 189B.

*Calyx*.—Shape: Star. Diameter: Approximately 2.4 cm.

*Sepals*.—Quantity per flower: 5 in a single whorl. Shape: Lanceolate. Apex: Acute. Base: Acute to truncate. Length: Approximately 1.7 cm. Width: Approximately 5.0 mm. Texture of upper and lower surfaces: Glabrous. Color of upper and lower surfaces: 138A.

*Peduncle*.—Strength: Moderately strong, flexible. Aspect: Acute angle to stem. Length: Approximately 9.4 cm. Diameter: Approximately 2.0 mm. Texture: Glabrous. Color: 144A.

*Reproductive organs*.—Androecium: Stamen quantity: 5 per flower, tightly appressed against ovary. Stamen length: Approximately 3.5 mm, two bear nectar spurs of approximately 3.0 mm in length. Anther shape: Ellipsoidal. Anther length: Approximately 3.0 mm. Anther width: Approximately 2.0 mm. Anther color: 155A with 165B at apex. Pollen amount: Sparse. Pollen color: NN155A. Gynoecium: Pistil quantity: 1 per flower. Pistil length: Approximately 5.0 mm. Stigma shape: Globular. Stigma length: Approximately 1.0 mm. Stigma color: 145B. Style length: Approximately 1.0 m. Style color: 145D. Ovary length: 3.0 mm. Ovary color: 145A.

Seed and fruit production: Neither seed nor fruit production has been observed.

Disease and pest resistance: Resistance to pathogens and pests common to *Viola* has not been observed.

What is claimed is:

1. A new and distinct cultivar of *Viola* plant named 'Halo Lemon Frost', substantially as herein illustrated and described.

* * * * *